United States Patent [19]
Wiegand

[11] Patent Number: 5,582,186
[45] Date of Patent: Dec. 10, 1996

[54] SPINAL ANALYSIS SYSTEM

[76] Inventor: Raymond A. Wiegand, 3104 Voltaire Blvd., McKinney, Tex. 75070

[21] Appl. No.: 237,629

[22] Filed: May 4, 1994

[51] Int. Cl.$^6$ .................................................. G01B 3/00
[52] U.S. Cl. .............................. 128/782; 128/774; 33/511
[58] Field of Search ...................................... 128/782, 774; 33/511, 512, 514.2

[56] References Cited

U.S. PATENT DOCUMENTS

| | | | |
|---|---|---|---|
| 2,295,447 | 9/1942 | Bierman | 33/514.2 |
| 3,196,551 | 7/1965 | Provost et al. | 128/774 X |
| 4,425,713 | 1/1984 | Rotella | 128/774 X |
| 4,823,476 | 4/1989 | Curtin | 33/512 |
| 5,080,109 | 1/1992 | Arme, Jr. | 128/782 |
| 5,329,933 | 7/1994 | Graf | 128/782 X |
| 5,337,758 | 8/1994 | Moore et al. | 128/782 X |

Primary Examiner—Sam Rimell
Attorney, Agent, or Firm—Ernest V. Linek

[57] ABSTRACT

A method for analyzing spinal characteristics of a patient believed to have one or more spinal abnormalities in which vertebral body rotations of the patient are determined for a plurality of spinal vertebrae and are graphically displayed along with vertebral body rotations of a normal person having no spinal abnormalities so that such displays can be readily compared to determine the locations of a patient's spinal abnormalities. Similar graphical displays of the differences in the relative rotational relationship of each vertebra and its superior neighboring vertebra can be provided for a patient and compared with graphical displays thereof for a normal person to identify locations of abrupt positional alignment changes representing spinal abnormalities Of the patient. Spinal stress unit values based on such vertebral rotations and rotational differences information, as well as on other selected parameters, can be determined for a patient with respect to successive treatments in order to provide a measurement of the progress of such treatments over time.

28 Claims, 9 Drawing Sheets

| | FLEXION | | | | | | EXTENSION | | | %IDEAL |
|---|---|---|---|---|---|---|---|---|---|---|
| | PATIENT | IDEAL | %IDEAL | 0 F | 2 DEG/DIV | 0 26 E | PATIENT | IDEAL | %IDEAL | DEF EXCUR | GLOBAL ROM |
| L1/L2 | 8.9 | 12.0 | 74 | | | | -7.7 | 6.0 | -128 | 4.4E | 49 |
| L2/L3 | 6.4 | 12.0 | 50 | | | | 1.0 | 6.0 | 22 | 1.9E | 43 |
| L3/L4 | 12.5 | 12.0 | 110 | | | | -0.6 | 6.0 | -10 | 6.3E | 75 |
| L4/L5 | 12.0 | 12.0 | 103 | | | | 3.1 | 6.0 | 52 | 3.1E | 86 |
| L5/S1 | -5.0 | 12.0 | -44 | | | | 7.7 | 6.0 | 128 | 15.4F | 43 |

PATIENT ▨  ▱ IDEAL —27

| LATERAL CERVICAL SEGMENTAL EXCURSION TOTALS | | | | |
|---|---|---|---|---|
| | | | | EXCURSION DISSYMMETRY |
| PATIENT | 41.1 | 12.1 | 53.2 | 31.6 |
| IDEAL | 60.0 | 30.0 | 90.0 | ? |
| %IDEAL | 68 | 40 | 59 | ? |

SEGMENTAL EXCURSION IS A MEASURE OF DISC-ANGLE CHANGE. AS SUCH, AN EXCURSION IS MEASURED IN DEGREES

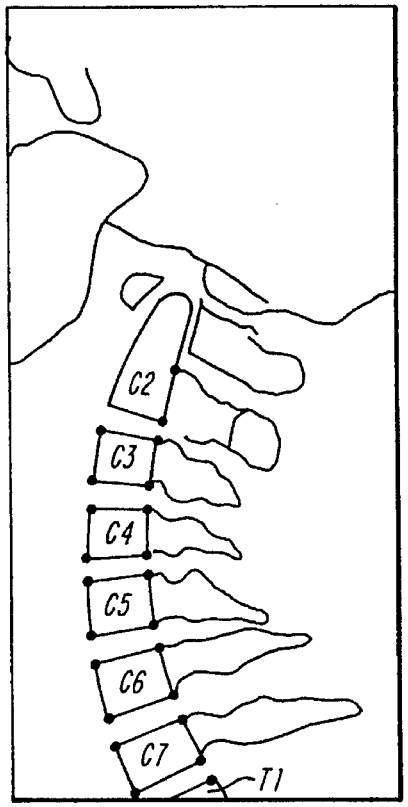

1. THE ANTERIOR AND POSTERIOR INTERSECTION OF THE CONDYLES WITH THE SKULL.

2. THE MID POINT OF THE ANTERIOR ARCH OF ATLAS.

3. THE MID POINT OF THE POSTERIOR ARCH OF ATLAS.

4. THE SUPERIOR INTERSECTION OF THE PEDICLE AND BODY OF C2

5. THE INFERIOR ANTERIOR POSITION OF THE BODY OF C2.

6. THE INFERIOR POSTERIOR POSITION OF THE BODY OF C2.

7. THE FOUR CORNERS OF THE VERTEBRAL BODY OF C3, C4, C5, C6, C7.

8. THE SUPERIOR ANTERIOR POSITION OF THE BODY OF T1

9. THE SUPERIOR POSTERIOR POSITION OF THE BODY OF T1.

*FIG. 16*

*CERVICAL PRE / POST*

|  |  | PATIENT | | RANGE | | % IDEAL | | SSU | |
|---|---|---|---|---|---|---|---|---|---|
|  |  | PRE | POST | AVERAGE | IDEAL | PRE | POST | PRE | POST |
| CEL< | (DEG) | 19.2 | 19.6 |  | 30.0 |  |  |  |  |
| CEL/CI< | (DEG) | 5.3 | 5.7 |  | 2.5 | 212 | 228 | 2.8 | 3.2 |
| CI< | (DEG) | 13.9 | 13.9 | 20.3 | 27.3 | 51 | 51 | 13.4 | 13.4 |
| C2< | (DEG) | -7.9 | -3.9 | 0.3 | 9.1 | -87 | -43 | 17.0 | 13.0 |
| CI/C2< | (DEG) | 21.8 | 17.8 | 19.7 | 17.9 | 122 | 99 | 3.9 | 0.1 |
| Rc | (cm) | -131.0 | -319.8 |  | 13.4 | -978 | -2387 |  |  |
| Rc up | (cm) | 23.5 | 50.8 |  | 13.4 | 175 | 379 |  |  |
| Rc lo | (cm) | 25.6 | 22.3 |  | 13.4 | 191 | 166 |  |  |
| Rc ideal | (cm) | 13.3 | 13.5 |  |  |  |  |  |  |
| CL<Rc | (DEG) | -18.7 | -13.2 |  | 0.0 |  |  | 18.7 | 13.2 |
| CL<Rc up | (DEG) | -21.3 | -13.8 |  | 0.0 |  |  |  |  |
| CL<Rc lo | (DEG) | -11.6 | -5.9 |  | 0.0 |  |  |  |  |
| SV< | (DEG) | 15.0 | 15.5 | 21.8 | 36.5 | 41 | 42 | 21.5 | 21.0 |
| SV |  | 3.8 | 4.6 | 3.9 | 4.9 |  |  |  |  |
| GC5 | (mm) | -16.5 | -9.4 |  |  |  |  | 16.5 | 9.4 |
| GC7 | (mm) | -31.5 | -21.1 |  | 0.0 |  |  | 31.5 | 21.1 |
| C4< | (DEG) | -22.1 | -14.9 |  | -10.0 |  |  | 12.1 | 4.9 |
| C7< | (DEG) | -29.0 | -25.0 |  | -27.0 | 107 | 93 | 2.0 | 2.0 |
| TI< | (DEG) | -24.5 | -25.0 |  | -30.0 | 82 | 83 | 5.5 | 5.0 |
| C2 DISC< | (DEG) | -0.6 | 4.1 | 3.8 | 6.6 | -9 | 62 | 7.2 | 2.5 |
| C3 DISC< | (DEG) | -4.2 | 0.0 | 4.5 | 6.7 | -63 | 0 | 10.9 | 6.7 |
| C4 DISC< | (DEG) | -1.6 | 2.2 | 3.1 | 7.2 | -22 | 31 | 8.8 | 5.0 |
| C5 DISC< | (DEG) | 3.5 | 1.3 | 2.4 | 4.2 | 83 | 43 | 0.7 | 2.4 |
| C6 DISC< | (DEG) | 0.0 | 2.3 | 2.7 | 4.2 | 0 | 55 | 4.2 | 1.9 |
| C7 DISC< | (DEG) | -4.4 | 0.0 | 1.5 | 2.0 | -220 | 0 | 6.4 | 2.0 |

CERVICAL SSU SUM

| PRE: | 183.1 |
| --- | --- |
| POST: | 126.8 |
| % CHG: | -31 |

SEVERITY

| PRE: | VERY SEVERE |
| --- | --- |
| POST: | SEVERE |

*1 SSU IS 1 UNIT (DEG/mm/cm) DIFFERENCE FROM IDEAL tt*

SPINAL STRESS UNITS

| SEVERITY | CERVICAL | THORACIC | LUMBAR | GLOBAL |
| --- | --- | --- | --- | --- |
| MINIMUM | 0 - 75 | 0 - 84 | 0 - 39 | 0 - 198 |
| MILD | 76 - 96 | 85 - 104 | 40 - 54 | 199 - 254 |
| MODERATE | 97 - 117 | 105 - 125 | 55 - 69 | 255 - 311 |
| SEVERE | 118 - 158 | 126 - 168 | 70 - 106 | 312 - 432 |
| VERY SEVERE | 159 - ? | 169 - ? | 107 - ? | 433 - ? |

*FIG. 17*

SPINAL ANALYSIS SYSTEM

INTRODUCTION

This invention relates generally to medical analysis techniques and, more particularly, to a unique method for analyzing spinal problems using computer data handling and display techniques and determining effective treatments from such analyses.

BACKGROUND OF THE INVENTION

The development of chiropractic spinal treatment techniques was initially based on mensuration, or measurement, methodologies which could identify the intersegmental disrelationships of one vertebra to another. Such methods were difficult, time consuming and did not allow for a cumulative evaluation over time of the entire spine and pelvis. Moreover, previous mensuration methodologies had no way to identify either regional (i.e., particular spinal regions) or global (i.e., the overall spinal column) compensation that is either normal or abnormal given certain geometric relationships.

The use of electromagnetic grids, primarily for display in computer aided drafting systems, has been developed and has generally become available for some time, e.g., since the 1970's. The use of such a technique has permitted the recording and digitizing of numerous data points in an x-y coordinate system and the supplying of such data points to a data processing system for the purpose of manipulating them to perform quantitative measurements therewith and to display such measurements in various ways on a display screen.

Though quantitative spinal measurements data have become easier and faster to obtain, no comprehensive analysis of such data has yet been made available so as to permit a chiropractic practitioner, for example, to determine, classify and distinguish between normal adaptive, i.e., successful, and abnormal nonadaptive, i.e., failed, compensation of the spinal/pelvic system. Moreover, the previous use of computer systems for spinal measurement has provided some, but inadequate, tabular data for use therein without providing any further insight into a spinal injury being examined. Accordingly, the chiropractic profession has generally tended to move away from the use of such computerized spinal mensuration techniques for clinical case management consideration and has failed to provide an effective technique for obtaining additional appropriately selected data and for analyzing such data in a manner which provides suitable insight into spinal problems so as to permit a practitioner to provide appropriate treatment and to teach the effectiveness of such treatment.

Hence, the problem of effectively selecting and analyzing spinal data still remains and it would be desirable to devise a more effective technique for using such data in order to determine, classify and distinguish between normal adaptive and failed compensation using computer aided techniques for the purpose of clinical case management consideration.

BRIEF SUMMARY OF THE INVENTION

In accordance with the invention, a spinal analysis process and system has been devised which allows for a systematic application of geometric measurements which, particularly when illustrated graphically, allow a relatively easy identification of failed spinal biomechanics for clinical case management consideration.

In accordance therewith, normal rotatory scoliosis, i.e., the adaptive mechanism of the spinal system to overcome structural deficiencies which can be recognized in an anterior to posterior (A/P) X-ray view, is used to present an x-ray with alternating convex curves. Each vertebral element rotates to the side of the convex curve in such a way that any gross, or subtle, intersegmental disrelationship tends to be minimized through a symmetrical distribution of structural misalignment throughout the entire spinal/pelvic system. The disc angle, i.e., the angle between adjacent vertebral elements also opens to the side of the convex curve.

It has been found that, by suitably evaluating the relationships among the convex curve, the vertebral body rotation and the disc angles involved, an appropriate sequential analysis can be used to identify normal and failed spinal compensation. Identifying statistically segmental, i.e., vertebral element, failures thereby provides the treating physician (e.g., a chiropractor) with the necessary information to provide corrective spinal manipulation to stabilize the patient's condition, i.e., primarily to reduce the pain associated with such failures. Moreover, evaluating patterns of segmental failures provides further insight into the extent and chronicity of spinal breakdown.

In accordance with an initial static measurement technique of the invention, selected data points on spinal A/P x-rays are appropriately recorded using an electromagnetic grid and utilizing known computer aided drafting techniques in a suitable data processing system. Appropriate data points on the x-ray are collected and supplied to a data processing system which is programmed to provide quantitative measurements using such data points and to provide a desired display thereof for spinal analysis.

When using data points obtained from an anterior to posterior x-ray view of the spine, for example, data analyses are provided by the data processing system, from which analyses segmental failure, regional adaptation and global compensation can be identified and assessed so that appropriate physical spinal manipulations can be applied in the A/P dimension.

In accordance therewith, the following various displays can be generated:

1) a graphical display of vertebral body rotation illustrated as proportional bar graphs related to each vertebral element, together with corresponding tabular measurements.

2) a graphical overlay display of ideal vertebral body rotations, also illustrated as proportional bar graphs.

3) a graphical display of intersegmental vertebral body counter rotations illustrated as proportional bar graphs, together with corresponding tabular measurements.

4) a graphical overlay display of ideal intersegmental vertebral body counter rotations illustrated as proportional bar graphs.

5) a combined graphical display of vertebral body rotation and intersegmental counter rotation illustrated as proportional bar graphs, together with copending tabular measurements.

6) a graphical display of intersegmental vertebral body counter rotations illustrated as proportional bar graphs, together with tabular measurements converted to a static quantitative spinal stress unit scale which when such measurements are made over time can be used to evaluate the patient's progress.

Further, dynamic measurements can be used in which data points obtained from spinal x-rays taken in the lateral dimension can be obtained during a neutral spinal mode, a flexion spinal mode and an extension spinal mode and supplied to the data processing system. The system appropriately manipulates the data points to determine the disc angles between adjacent vertebral elements for each mode, so as to depict the dynamic changes therein that occur between modes. The symmetries or dissymmetries in disc angle change from the neutral disc angle values, particularly in the cervical region of the spine as well as in the lumbar region thereof, can be initially displayed and compared with an ideal dynamic symmetry. Any failures in the lateral dimension can be recognized and regional adaptations can be identified and assessed so that appropriate physical spinal manipulation can be applied in the lateral dimension. Further data can be obtained from the data points with respect to other spinal parameters which can then be converted to a dynamic quantitative stress unit scale which when such measurements are made over time can be used to further evaluate the patient's progress.

DESCRIPTION OF THE INVENTION

The invention can be described in more detail with the help of the accompanying drawings wherein FIG. 1 illustrates diagrammatically an exemplary vertebra;

FIG. 16 depicts exemplary osseous spinal landmarks used in accordance with a method of determining progress of treatment of a patient; and FIG. 17 shows exemplary tabulations for selected parameters derived using said osseous landmarks for determining spinal stress unit values for tracking the progress of the treatment of a patient.

Figure 1:
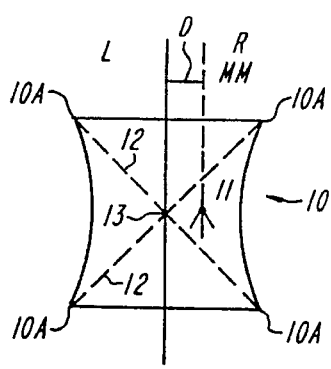

FIG. 1 depicts a simplified diagram which can be used to illustrate what is meant by vertebral body rotation, as would be well known to those in the art. As seen therein, vertebral body rotation is measured by identifying four corners 10A and an interlamina junction point 11 of a vertebra 10 depicted in a simplified form in an anterior/posterior (A/P) dimension x-ray image. If diagonal lines 12 are drawn from opposing corners, the intersection location 13 thereof represents the theoretical center of the vertebra. The horizontal distance D from a line through the theoretical center 13 to a parallel line through the interlamina junction 11 represents the rotation of the vertebral body. The corner points 10A and the junction point 11 can be supplied to a data processing system and, using well known computer aided drafting techniques, the data processing system can perform the desired handling of the data so as to determine the intersection location 13 and the distance D for each vertebra of the overall spinal column and so as to represent such distance as a proportional horizontal bar graph.

The linear distance D is in fact an arc length traversed by the interlamina junction as the vertebral body rotates from its theoretical center. Thus, while it is not entirely accurate to refer to this distance, normally expressed in millimeters, as a "rotation", the linear distance in effect represents a proportional measurement of vertebral body rotation. Accordingly, for convenience in understanding the concept, the vertebral movement is often referred to by those in the art as "rotation" rather than as "arc length" traversed. Thus, for the sake of understanding and perception the term rotation is used herein instead of "arc length" and such distance is recorded in millimeters rather than in degrees of rotation.

Figure 2:
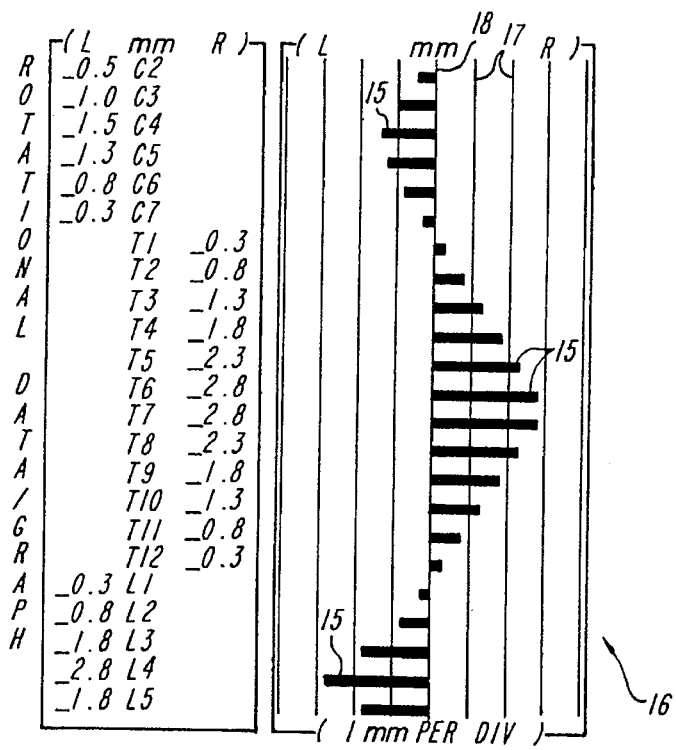
FIGS. 2 and 3 show displays in bar graph form of exemplary normal and abnormal left vertebral rotations.

Each vertebra is measured in a similar fashion and the individual rotations can be displayed by the data processing system in a global coherent bar graph representation. As used herein the term "global" is used to mean that the display includes cervical, thoracic and lumbar regions of the overall spine configuration. The data processing system can also display such information in tabular form. The results of a typical global bar graph and tabular display technique are illustrated in FIG. 2. The methodology used to display a global representation can also be used to display only individual regions of the spine if desired.

As shown in FIG. 2 for a left compensating pattern, the rotation of each vertebra as illustrated by the bars 15 can be superimposed on a vertical grid 16 which includes grid lines 17 having a known distance therebetween, a typical grid line separation being 1.0 mm., for example. The display of such a grid and such superimposition of data illustrated by bars thereon, is also well within the skill of the art of computer aided drafting techniques in other contexts. Hence, using such techniques vertebral rotations can be displayed at the left (L) and right (R) of a center grid line 18. The rotation distances and directions thereof are also tabulated and displayed as shown at the left of FIG. 2, also using well-known data processing tabulation techniques, for cervical vertebrae C1–C7, thoracic vertebrae T1–T12 and lumbar vertebrae L1–L5, respectively.

Viewing the vertebral body rotations in either a regional or a global perspective as shown in FIG. 2 permits the viewer to easily identify a rotational discontinuity of one vertebra with its superior or inferior neighbor and thus permits a static segmental assessment of the vertebrae on a regional or global basis.

The measurement and graphical display technique permits any abrupt disrelationship of one vertebra to another to be readily identified and permits a ready determination of how that malposition compares to other vertebrae within the spinal region. This display technique allows the treating physician to easily identify discontinuities in rotation and to decide on a clinical course of corrective treatment to stabilize the patient. Thus, while FIG. 2 depicts an exemplary graphical presentation of a generally normal or ideal positioning of the vertebrae, FIG. 3 depicts an exemplary graphical left compensatory pattern of an abnormal positioning thereof, wherein the rotations of certain vertebrae, e.g., C4, T1 and L4, are clearly discontinuous with respect to their adjacent vertebrae.

Figure 3:
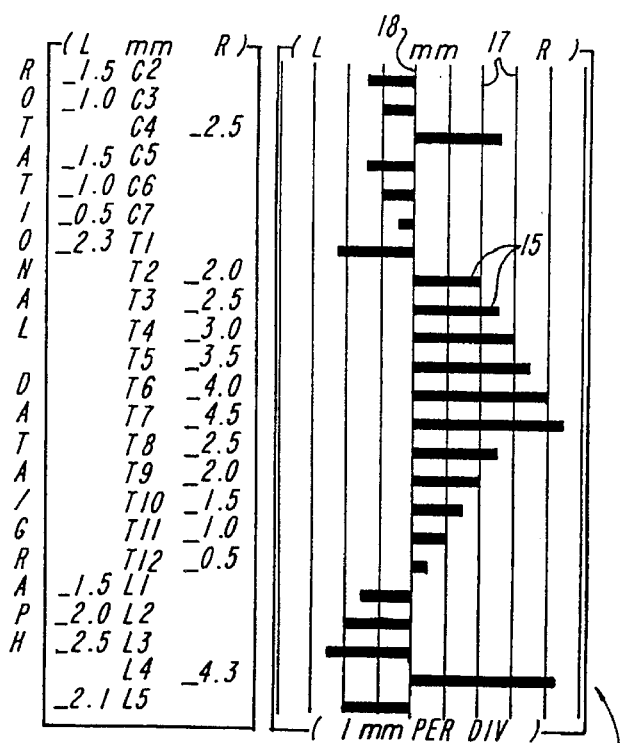

Given a condition of compromise, or deviation, from the ideal architectural alignment of the spinal system, such as shown in FIG. 3, there exists a functional compensatory distortion pattern of vertebral body rotation which can minimize the intersegmental disrelationships which are present, while symmetrically distributing the body weight to the left and right of a true spinal centerline. This compensatory pattern of ideal rotation occurs in normal rotatory scoliosis which is an exaggeration due to a structural deficiency.

Figure 4:
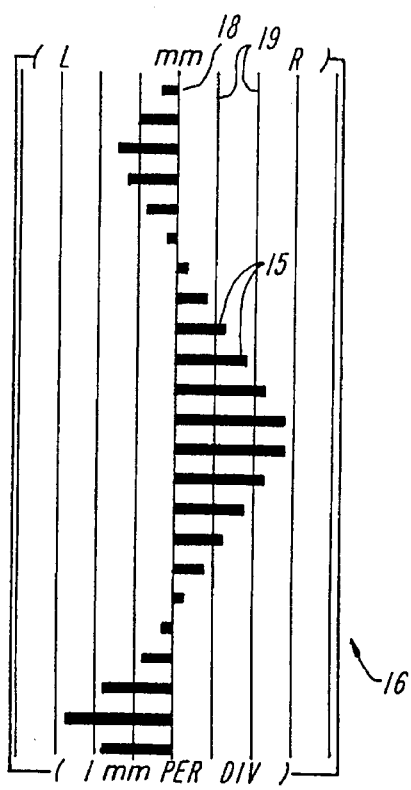
FIGS. 4 and 5 show displays in bar graph form of exemplary normal left and right vertebral rotations.
Figure 5:
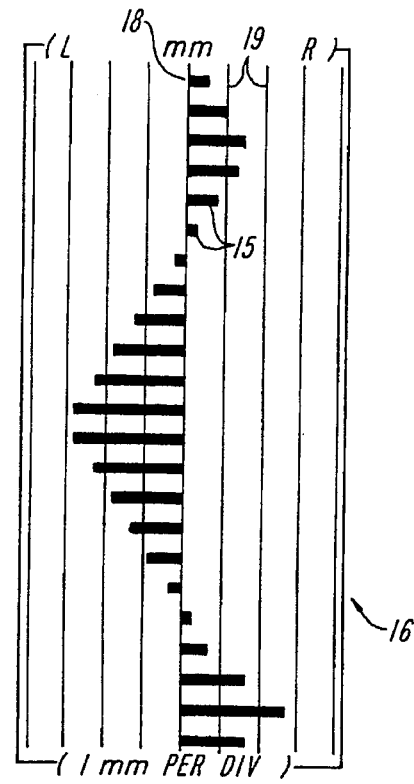

An ideal stable left compensatory pattern of vertebral body rotations, i.e., derived from an x-ray taken from the A/P dimension is illustrated by FIG. 4 (the same as in FIG. 2), while an ideal stable right compensatory pattern of vertebral body rotations, is illustrated in FIG. 5. These stable compensatory patterns will occur in response to a unilateral inferior sacrum, or any deficiency which compromises ideal alignment.

In accordance with the spinal analysis process of the invention, an overlay of a right or left ideal compensatory pattern on an actual compensatory pattern can be used to assess the adaptive state of the patient's spinal system, by matching the ideal pattern to the patient's rotation pattern.

While up to now no analysis has been devised to compare a patient's vertebral body rotations to ideal compensatory/stable patterns, such a graphical overlay technique in accordance with the invention permits a treating physician to more readily identify departures of vertebral body rotations which do not minimize the global intersegmental disrelationship. A graphical presentation as used in accordance with the invention makes more clear to a treating physician what clinical course of treatment should be initiated to return the spine to a minimal compensatory pattern, such an assessment not being previously possible without the analysis approach of the invention.

Figure 6:
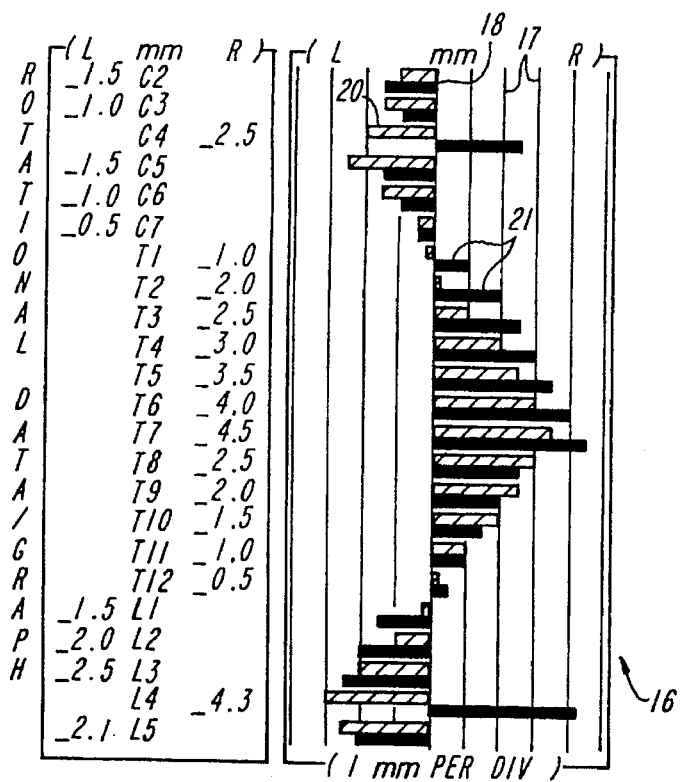
FIG. 6 shows a display of superimposed bar graphs of normal and abnormal left vertebral rotations.

A clinical example of such overlay display technique, generated by using well-known computer display techniques is illustrated in FIG. 6. An ideal compensatory pattern is depicted by the cross-hatched pattern bars 20 while a patient's actual rotation pattern is depicted by solid pattern bars 21. The graphical presentation permits the actual and ideal patterns to be readily compared. Thus, in the exemplary patterns depicted, the clinical solution to the patient's distorted pattern would be to rotate vertebra C4 to the left and vertebra L4 to the left. Such rotation would then return the patient to a balanced minimal compensatory pattern. The amplitudes of the displayed ideal rotation need not be related to the amplitudes of the displayed actual rotations since only a general comparison of the overall wave shape configuration is needed to permit readily perceived departures from the ideal. Such an assessment can be made without superimposing the ideal and actual bar graphs (as with FIG. 3) although such superimposition has been found helpful in making such a wave shape comparison.

In as much as the required rotation of individual vertebra can be demonstrated as discussed above, such analysis may be subject to the effects of patient positioning as it relates to x-ray distortions that may occur in generating data for use in the graphical presentations. The effects of such distortions on the linear measurements involved can be minimized by further investigating the intersegmental rotational relationship. It is found that, by measuring the vertebral intersegmental rotational relationship, i.e., the rotation as it changes from one vertebra to an adjacent vertebra, more consistent information can be provided even when the initial patient position changes. Thus, the relative rotational interrelationship from one vertebra to another, which will be referred to below as the counter rotation, may be measured more accurately even with patient movement to provide further data for clinical case management consideration.

The counter rotation of one vertebra to another is determined in the following manner. From data obtained in x-rays in the left and right A/P dimensions, the rotation of an inferior vertebra and the rotation of a superior vertebra (the next adjacent upper vertebra) are determined, as above, and, in the data processing system, the rotation value of the inferior vertebra is subtracted from that of the superior vertebra so as to provide a relative rotational difference of the inferior vertebra as compared to its superior neighbor. Either the superior or the inferior vertebra may be used as the reference.

Figure 7:
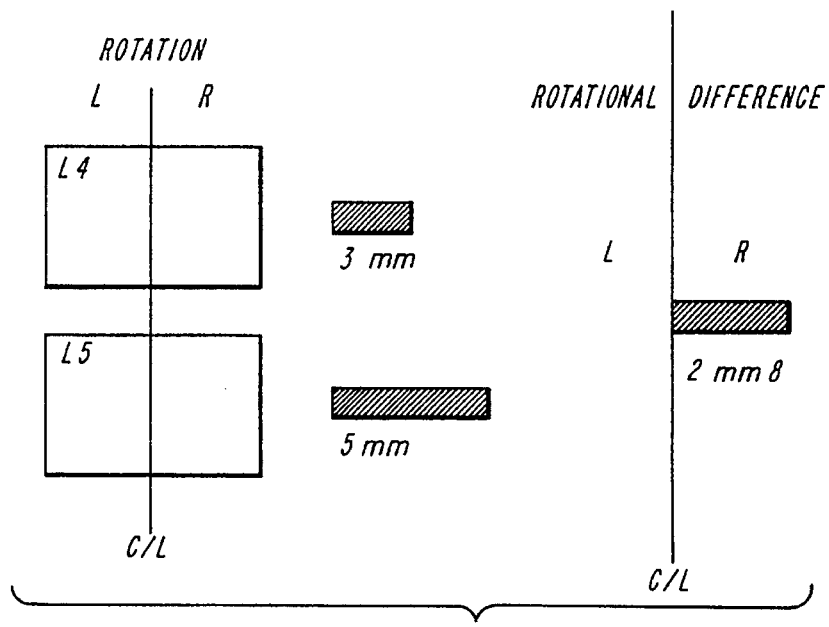
FIG. 7 shows diagrammatically an exemplary vertebral rotational difference between adjacent vertebrae.

The pattern of rotational differences can then be displayed as a proportional bar graph for each intersegmental level. FIG. 7 illustrates in a simplified manner the methodology and graphing involved. In the example shown, inferior vertebra L5 is rotated 2 mm to the right of superior vertebra L4, where L4 is rotated 3 mm right and L5 is rotated 5 mm right so that the difference is 2 mm.

Figure 8:
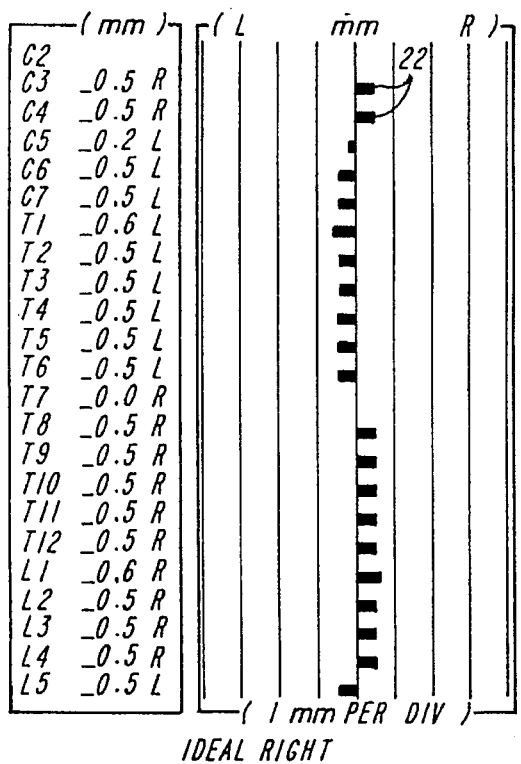
FIGS. 8 and 9 show displays in bar graph form of exemplary normal right and left vertebral rotational differences.
Figure 9:
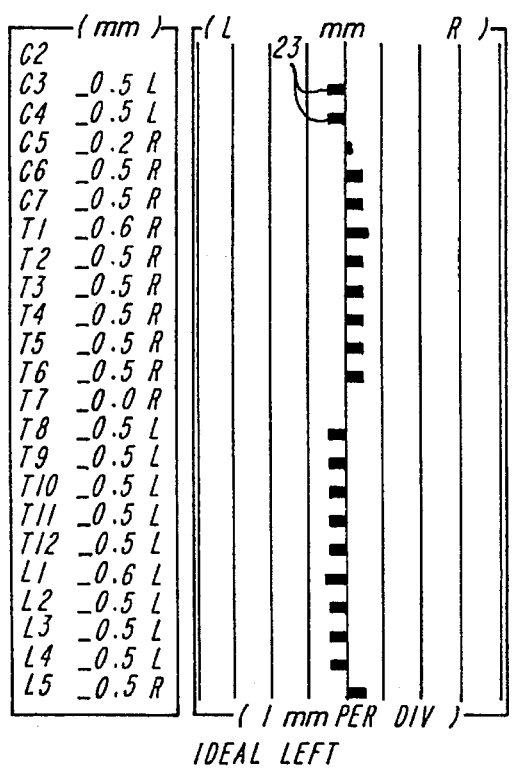

An ideal compensatory pattern for vertebral body rotations dictates that the intersegmental disrelationships be minimized throughout the global spinal system in accordance with the ideal adaptive rotations shown in FIGS. 4 and 5. FIGS. 8 and 9 illustrate the tabular and graphical patterns of bar graphs 22 and 23 of global right and left ideal intersegmental counter rotation patterns, respectively, i.e., intersegmental rotational differences which exist in ideal adaptive compensation. Other patterns may exist which illustrate either a breakdown of the primary compensatory pattern or that the spine is in a pre compensatory state. In the ideal patterns shown in FIGS. 8 and 9, the inferior vertebra is being compared to its superior neighbor.

Up to now, no analysis has been available which evaluates abrupt positional changes of intersegmental alignments and at the same time minimizes the effects of patient positional changes and possible x-ray distortions. Viewing a patient's intersegmental counter rotations, both regional and global, as proportional horizontal bar graphs, in accordance with the invention, allows an easy identification of such abrupt positional alignment changes.

Figure 10:
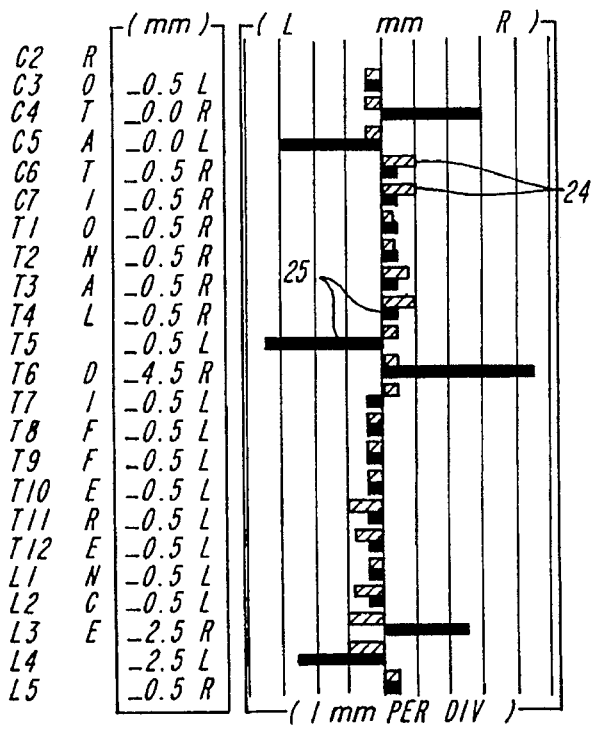
FIG. 10 shows a display of superimposed bar graphs of exemplary normal and abnormal left vertebral rotational differences.

FIG. 10 illustrates an exemplary display of a patient counter rotation bar graph, devised in accordance with the process discussed with reference to FIG. 7 as discussed above. FIG. 10 further includes an overlay of ideal left intersegmental counter rotations, such as shown by the cross-hatched bars 24 and the actual exemplary counter rotations in a patient, such as shown by the solid bars 25, in FIG. 10. The intersegmental levels of the highest bar graph values identify where adaptive rotational compensation has failed. In the example shown, counter rotation failure occurred at C4, C5, T5, T6 and L3, L4. The treating physician can immediately identify such failures from the ideal adaptive compensation using this counter rotation method of analysis wherein such an overlay comparison can be made. Thus, the information contained in the comparison analysis of FIG. 10 makes more clear to the treating physician where specific spinal treatment is required.

Figure 11:
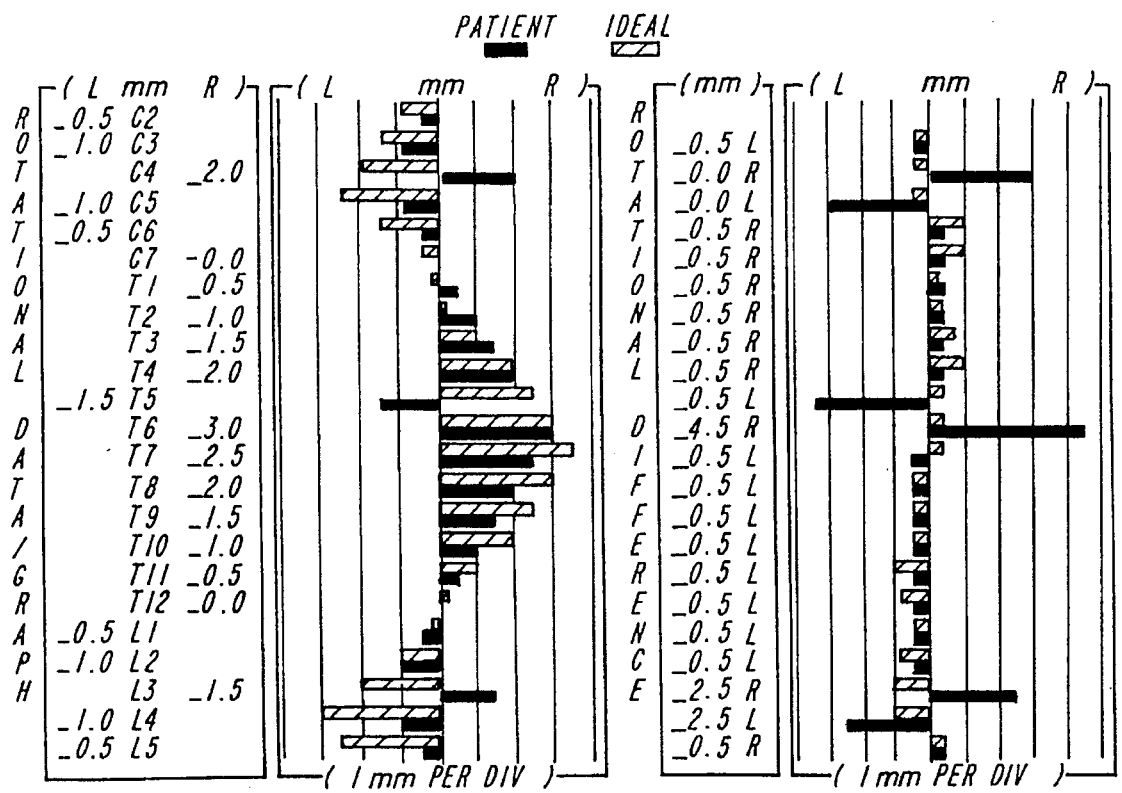
FIG. 11 shows a combined display in bar graph form of exemplary superimposed left normal and abnormal vertebral rotations and exemplary normal and abnormal left vertebral rotational differences.

The combined information provided by a vertebral body rotational comparison graph (e.g., FIG. 6) and by a vertebral body counter rotational (difference) comparison graph (e.g., FIG. 10) makes clear the determination of where maximum rotational stress is occurring and where adaptive compensation has failed in the spinal system. FIG. 11, for example, illustrates a display of combined vertebral body and counter rotational comparison analysis, which can be generated and placed simultaneously on a display for the treating physician.

The counter rotational graph at the right of the display identifies clearly the levels of highest rotational stresses while the rotational graph at the left thereof identifies a failure relative to normal adaptive compensation. The disrelationships involved can be corrected by the treating physician using the exemplary graphs of FIG. 11 by rotating vertebra C4 to the left, T5 to the right and L3 to the left. By correcting the rotational aberrations one corrects the failure relative to adaptive compensation in the A/P dimension using such static measurements and display.

Figure 12:
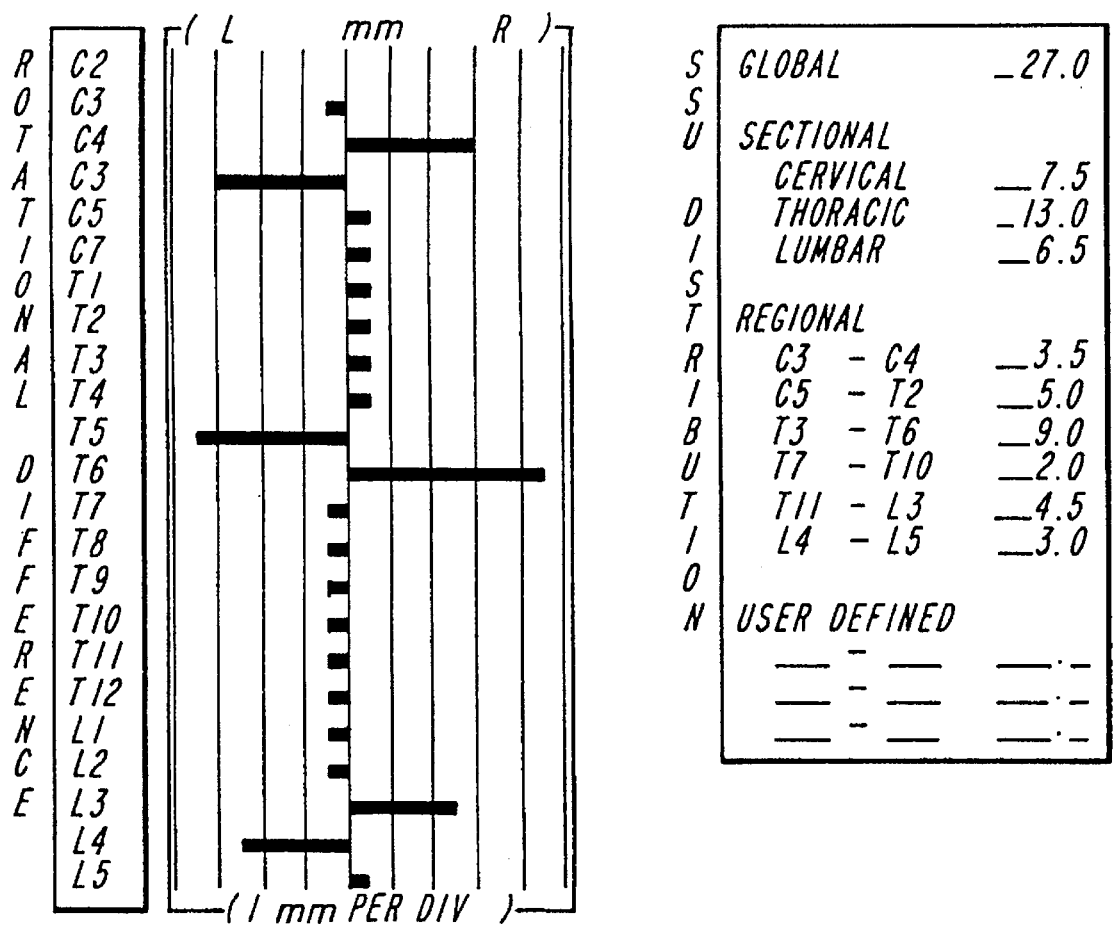
FIG. 12 show an exemplary bar graph display of exemplary left abnormal vertebral rotational differences and a tabulation of exemplary spinal stress unit values derived therefrom.

The intervertebral counter rotational (difference) analysis is a direct measurement of rotational stress on the spinal system. Rotational stress distribution can be assessed for its symmetry with respect to global compensation. FIG. 12, for example, illustrates a display of an exemplary tabular sum of the global (i.e., all three spinal regions combined), the regional (for all three regions separately) and specific regional ranges (for specified portions within a region or overlapping of two regions) of the counter rotational or difference measurements shown by the bar graph in FIG. 12 (which is the same as that shown in FIG. 10). In the example shown, one millimeter of counter rotation is assigned the value of one spinal stress unit (SSU).

A global spinal stress unit scale number can be obtained by adding the spinal stress calculated unit for each of the spinal regions, e.g., 27.0 in FIG. 12. Such scale number allows an objective quantitative assessment of spinal rotational stress and symmetry. A series of such assessments taken over time throughout treatment can be compared so as to identify the response and effectiveness of spinal adjustment procedures and support modalities that have been used in treatment, i.e., to track the patient's treatment progress, e.g., the SSU number should decrease as successful treatment proceeds. Such an objective number which can be used to track rotational symmetry of the spine has not been previously available for ready investigation by a treating physician.

In summary, the spine can be evaluated in the A/P dimension through the use of a static graphical analysis technique by which the vertebral body rotation and intersegmental counter rotations can be effectively computed and displayed. The analysis uniquely identifies a failure to achieve ideal compensation and assists the treating physician in determining a clinical course of treatment. A series of x-rays can be quantitatively analyzed and compared over time to produce an objective spinal stress unit (SSU) score to permit a continued assessment of active treatment intervention.

A similar dynamic methodology of analysis can be applied to the evaluation of the inter-vertebral disc angles of the spine as determined from x-rays in the lateral dimension. A disc angle is the angle of the region between adjacent vertebrae in which a spinal disc resides, as shown in the simplified idealized diagram of FIG. 13. As seen therein the extended lines 30 and 31, respectively drawn between the lower corners of a superior vertebra 32 and the upper corners of an inferior vertebra 33 form a disc angle 34, a disc (not shown) residing between the vertebrae.

With such corner data points obtained from a lateral dimension x-ray, the computer can calculate all of the disc angles for the cervical vertebrae, for example, using well-known computer aided drafting techniques, and can display such calculated disc angles as a proportional horizontal bar graph for each cervical vertebral level. A normal disc angle for each vertebral level can be generated for a normal convex curve of the cervical region and such normal disc angles can also be displayed for the cervical region so that they can be overlaid and compared with the patient's calculated disc angles. Such normal disc angles can be generated from previous known studies of lateral dimension x-rays and, in effect, are derived as average disc angles from a large number of normal patients, i.e., patients not known to be suffering from cervical vertebral dislocation, when the patients are in a neutral spinal mode, i.e., the spine is in a vertical, non-flexed and non-extended position.

Similar disc angles can also be calculated from a patient's lateral dimension x-ray for the lumbar and thoracic regions. Average disc angles from studies of a large number of normal patients can be generated for comparison.

The integrity of intersegmental cervical mobility can be evaluated by assessing the amount of angular change that occurs between the neutral and flexion modes and between the neutral and extension mode. Such measurements have been investigated by others for a normal, i.e., an uninjured, population, for example, in the article Journal of Neuroradiology, "Radio-Functional Analysis of the Cervical Spine using the Arlen Method"; Kramer, M., 1989. Such article reported findings that indicate an approximate 1:1 ratio of angular change between C1/C2, C2/C3, C3/C4, C4/C5, and C5/C6 and a 2:1 ratio for C6/C7. A 2:1 ratio is assumed for C7/T1.

Figure 14:
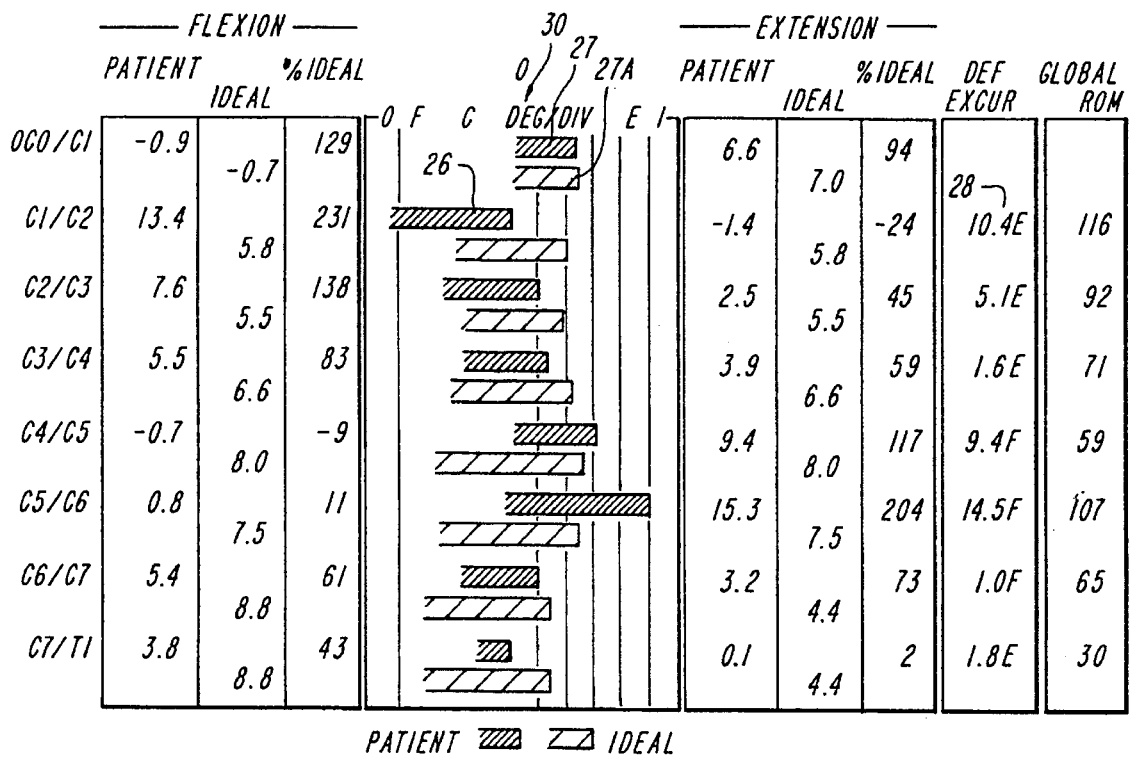
FIGS. 14 and 15 show displays in bar graph form of changes in disc angles for flexion and extension modes for an exemplary patient and exemplary tabulations of intersegmental motions derived therefrom for the cervical and lumbar regions, respectively.

In accordance with the invention, intersegmental disc angle change is calculated as discussed above for flexion and extension for each cervical motion segment and the values are displayed using bar graphs to compare the patient to normal values. FIG. 14 shows angular change or displacement values 26 for flexion and values 27 for extension as illustrated from a centerline 30. The normal intersegmental range of motion is illustrated with hatched bar graphs 27A. Further, the range of motion (referred to in FIG. 14 as ROM) can also be calculated as a percentage of ideal ROM for flexion, extension and flexion plus extension for the individual motion segments.

Intersegmental motion is evaluated by taking the difference between the flexion and extension values. When a motion segment is functionally intact, predictable motion occurs. Aberrant motion ratios indicate a functional neutral fixation equal to the amount of flexion or extension difference, 28 (FIG. 14).

Patient values for all the motion segments can be combined (FIG. 14) to evaluate global flexion 29, extension 29A, flexion plus extension 29B and intersegmental motion dissymmetry 29C. The global patient values are expressed as a percentage of ideal values 29D.

The neutral fixation value can be used to evaluate which segment is most functionally disrupted and what line of correction (referred to as LOC) is needed for treatment consideration. A deficient excursion in extension (E) requires an inferior to superior LOC while a deficient excursion in flexion (F) requires a superior to inferior LOC.

The measurement and display of intersegmental motion in the lateral dimension uniquely identifies a failure to achieve normal adaptive compensation. It quantitatively identifies motion segment dysfunction for treatment consideration. It compares the patient to ideal angular displacements by overlay and tabular calculation techniques and quantitatively identifies each segmental dysfunction as a flexion or extension fixation. Segmental and regional ROM can be accurately determined.

An exemplary analysis of the dynamic situation for the cervical region depicted in FIG. 14 would indicate that the occiput is substantially fixed in flexion and would require a superior to inferior (LOC) to correct its neutral position. C1 is fixed in extension and would require an inferior to superior LOC to correct its neutral position.

Figures 13, 15:
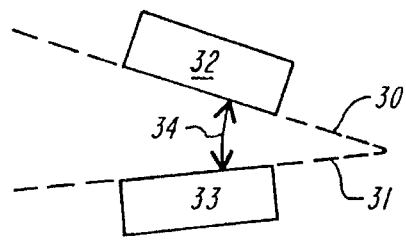
FIG. 13 shows diagrammatically an exemplary disc angle between adjacent vertebrae.

A similar exemplary display of disc angle calculations for the lumbar region is depicted in FIG. 15. An exemplary analysis of the dynamic situation depicted in FIG. 15 would indicate that LS/S1 is fixed in flexion and would require a superior to inferior LOC to correct their neutral positions.

While a similar display can be provided for the thoracic region, this analysis is not performed as the thoracic region has very little flexion and extension due to the rib cage. However, if needed, it can be performed using the same techniques discussed above.

In addition to a static global spinal stress unit scale, in the A/P dimension, as already discussed above, a lateral dimension dynamic spinal stress unit, or value, can be generated in the lateral motion study so as to track a patient's progress over time.

In order to track a patient's progress as treatment based on the above analysis is pursued, it is desirable to provide an objective criterion, i.e., an objective value, or values, that can be calculated periodically over a treatment time period to determine if the treatment has produced, and is continuing to produce, desired results. In accordance with the invention, an objective spinal stress unit value for each spinal region, as well as a global spinal stress unit value representing a combination thereof, has been developed using a plurality of appropriately selected parameters which can be determined from a measurement of specifically defined osseous landmarks in each of lateral spinal regions.

Osseous landmarks for the cervical spinal region as shown in FIG. 16 are determined using lateral cervical X-rays. The landmarks illustrated in the figure are identified as follows:

1. the anterior and posterior intersection of the condyles with the skull.
2. the mid point of the anterior arch of atlas.
3. the mid point of the posterior arch of atlas.
4. the superior intersection of the pedicle and body of C2.
5. the inferior anterior position of the body of C2.
6. the inferior posterior position of the body of C2.
7. the four corners of the vertebral body of C3, C4, C5, C6, C7.
8. the superior anterior position of the body of T1.
9. the superior posterior position of the body of T1.

The x-ray is placed on an electromagnetic grid and the coordinates of the osseous landmarks are recorded. Using appropriate and known graphical software, the coordinates of the patient x-ray are suitably processed to provide a geometric model of the cervical spine so that a graphic image thereof is rendered, as illustrated in FIG. 16. The patient data points with respect to cervical vertebrae are stored for retrieval to calculate the following lateral cervical measurements:

LATERAL CERVICAL MEASUREMENTS

CDL<: Condylar Angle (deg)/Plane line of the occiput

This parameter represents a reference position of patient placement in accordance therewith the following two points (See FIG. 16) are located and a line is drawn and compared to a true horizontal.

Point 1. anterior occipital condlyle and skull intersection

Point 2. posterior occipital condyle and skull intersection

With respect to this reference position, a neutral placement position is 30 degrees to the horizontal. C1<: C1 Angle (deg)

This parameter represents the angle of atlas plane line to the horizontal. A neutral position is approximately 27 degrees in extension. In accordance therewith the following two points are located and a line is drawn and compared to a true horizontal.

Point 1. The vertical distance of the anterior arch of atlas is measured and bisected Point 2. The vertical distance of the posterior arch is measured and bisected.

Clinically, an increased angle indicates a fixed extension of C1 and a posterior displacement of the head weight, while a decreased angle indicates fixed flexion of C1 and an anterior displacement of the head weight.

CDL/C1<: Condylar/C1 Angle (deg)

This parameter represents the interangular relationship of the plane line of the condyles and the atlas plane line. Neutral position is 2.5 degrees facing the anterior (extension). Clinically, diminished or reversed angulation is suggestive of fixed flexion of the occiput and an anterior displacement of the head weight, while increased angulation indicates a fixed extension of the occiput and a posterior displacement of the head weight.

C2<: C2 Angle (deg)

This parameter represents the angle of C2 compared to the horizontal using a perpendicular to the posterior C2 body. A neutral position is 10 degrees in extension. The following two points are connected to form a line AB.

Point 1. Superior posterior body of C2 at pedicle junction

Point 2. Inferior posterior body of C2

A perpendicular is drawn from line AB and is compared to a true horizontal. Clinically, a decreased angle causes anterior displacement of the head weight, loss of upper cervical curve and anterior weight bearing to the entire cervical curve; while an increased angle causes posterior displacement of the head weight, an increase in the upper cervical curve and an increased loading to the posterior pillar.

C1/C2<: C1/C2 Angle (deg)

This parameter represents the inter-relationship of the atlas plane line to the C2 body perpendicular. A neutral position is 18 degrees in extension. Clinically, an increased angle indicates a C1 fixed in extension and a posterior displacement of the head weight, while a decreased angle indicates a C1 fixed in flexion and anterior displacement of the head weight.

Rc: Radius of Curvature; Overall (cm)

Thus, the radius parameter is a measure of the cervical curvature using three points located on the posterior superior bodies of C2, C5 and T1. In the neutral position the ideal radius RcI is determined by equilibrating RcI to the chord distance measured from anterior C1 (point 1 of atlas plane line) to the posterior superior body of T2. Clinically, a loss of curvature (increased radius of curvature; hypolordotic) in combination with fixed flexion results in an increased loading to the anterior pillar. An anterior loading is a causative factor in accelerated anterior pillar (disc and vertebral body) degeneration. An anterior loading results in separation of the posterior (facet) joints leading to hypermobility. A gain of curvature (decreased radius of curvature; hyperlordotic) causes increased loading onto the posterior pillar (facet joints). A posterior loading causes facet jamming and hypomobility.

RcU: Radius of Curvature; Upper (cm)

The radius of curvature of the upper cervical curve is measured using three points located on posterior superior bodies of C2, C3, C4. The upper radius is compared to the ideal and measured radius. When the cervical curve is coherent the upper radius approximates the overall radius (Rc) of curvature. A difference of the upper and lower radius to the measured radius is suggestive of ligamentous disruption or dysfunction. Clinically, an increased radius of curvature (hypolordosis) causes increased loading to the anterior pillar when accompanied with a centerline angle in fixed flexion; while a decreased radius of curvature (hyperlordosis) causes increased loading to the posterior pillar. Abnormal facet loading occurs with a non coherent curve particularly in the presence of fixed extension.

RcL: Radius of Curvature; Lower (cm)

The radius of curvature of the lower cervical curve is measured using three points located on the posterior superior bodies of C5, C6, C7. The lower radius is compared to the ideal and measured radius. When the cervical curve is coherent the lower radius approximates the measured radius (Rc) of curvature. A difference of the upper and lower radius to the measured radius is suggestive of ligamentous disruption or dysfunction. Clinically, an increased radius of curvature (hypolordosis) causes increased loading to the anterior pillar particularly in the presence of fixed flexion of the centerline angle. A decreased radius of curvature (hyperlordosis) causes increased loading to the posterior pillar. An abnormal facet loading occurs with a non coherent curve particularly in the presence of fixed extension of the centerline angle.

CL<Rc: Centerline Angle of the Radius of Curvature (cm)

This parameter represents the centerline angle of the radius of curvature and is a measure of fixed extension (+angle) or flexion (−angle) of the cervical curve. The curve centerline is drawn from the points (1) the curve focus and (2) the center of the curve. The curve centerline is compared to a true horizontal. Clinically, fixed flexion of the centerline angle results in anterior weight bearing of the skull throughout the entire cervical curve with maximum torsional loading at C7/T1. The head and neck extensors are in chronic reactive contraction and fatigue.

CL<RcU: Centerline Angle of the Upper Radius (cm)

This parameter represents the centerline angle of the upper radius of curvature is a measure of fixed extension (+) or flexion (−) of the upper cervical curve. The curve centerline is drawn from the points (1) the upper curve focus and (2) the center of the upper curve. The upper curve centerline is compared to a true horizontal. Clinically, fixed flexion results in increased loading to the anterior pillar, C2 flexion and reactive C1 extension. The head and neck extensors are in chronic reactive contraction. Fixed extension results in posterior weight bearing of the head with increased posterior pillar loading.

CL<RcL: Centerline Angle of the Lower Radius (cm)

This parameter represents the centerline angle of the lower radius of curvature is a measure of fixed extension (+) or flexion (−) of the lower cervical curve. The centerline is drawn from the points (1) the lower curve focus and (2) the center of the lower curve. The lower curve centerline is compared to a horizontal. Clinically, fixed flexion results in increased loading of the anterior pillar and reactive C1 extension. The neck extensors are in chronic reactive contraction, while fixed extension of the lower cervical curvature results in increased posterior pillar loading.

SV<: Stress Vertebra Angle (deg)

This parameter represents the stress vertebra line intersection and is a measure of the integrity of the cervical curve. Lines are drawn off the posterior bodies of C2 and C7. The normal angle of intersection is 38–43 degrees. Clinically, diminished angulation represents hypolordosis with resultant increased anterior pillar loading and separation of the facet joints particularly when in combination with fixed regional flexion. Increased angulation represents hyperlordosis with resultant increased posterior pillar loading and jamming of the facet joints particularly when in combination with fixed regional extension.

SV: Stress Vertebra (scale of ten divisions)

This parameter represents the stress vertebra and is the location of intersection of the cervical stress lines. The normal location of intersection is at the C4/C5 disc interspace. The vertebra body is divided into 10 equal divisions and reported as ex. C4.9 (i.e., the intersection occurs 9/10th of the way down the C4 vertebral body. Clinically, intersection of cervical stress lines other than C4/C5 indicates abnormal increased segmental loading at that location.

GC5: Gravity transfer at C5 (mm)

This parameter represents a horizontal measure of the head weight as it is projected vertically downward from posterior superior body of C2 as it passes by the posterior superior point of the C5 vertebral body. In an intact cervical curve the head weight passes posterior to the C5 reference point. As the curve destabilizes through loss of curvature or fixed flexion, the head weight passes anterior of the C5 reference point. Clinically, anterior positioning of the head weight creates abnormal loading to the anterior pillar of the cervical curve. Increased torsional stresses are in direct proportion to the anterior linear displacement of GC5. Anterior weight bearing causes posterior joint separation and abnormal ligament loading. Anterior loading is a known degenerative accelerator to the anterior pillar (disc and vertebral body).

GC7: Gravity transfer at C7 (mm)

This parameter represents a horizontal measure of the head weight as it is projected vertically downward from posterior superior body of C2 as it passes by the posterior superior point of the C7 vertebral body. In an ideal intact cervical curve the head weight passes through the C7 reference point. Clinically, as the head weight passes anterior to the reference point increased torsional loading occurs at C7/T1 which is directly proportional to the anterior linear displacement. Anterior weight bearing causes posterior joint separation and abnormal ligament loading. Anterior loading and posterior joint separation is a known degenerative accelerator to the anterior pillar of the motion segment.

C4<: C4 Vertebral Angle (deg)

This parameter is measured by comparing a line drawn from the inferior plate of C4 intersecting with a horizontal. The normal value is 5 degrees in flexion. The C4< demonstrates the positional integrity of the base of the upper cervical radius of curvature. Clinically, a decreased value would indicate a segmental positioning failure resulting in fixed flexion of the upper radius, while an increased value would indicate a segmental positioning failure resulting in fixed extension of the upper radius.

C7<: C7 Vertebral Angle (deg)

This parameter is measured comparing a line drawn from the inferior plate of C7 intersecting with a horizontal. The normal value is 27 degrees in flexion. The C7< demonstrates the positional integrity of the base of the lower cervical radius of curvature. Clinically, an increased flexion value would indicate a segmental positioning failure resulting in fixed flexion of the lower cervical radius of curvature, while an increased extension value would indicate a segmental positioning failure resulting in fixed extension of the lower cervical radius.

T1<: T1 Angle (deg)

This parameter is measured comparing a line drawn off the superior plate of T1 intersecting with a horizontal. The normal value is 30 degrees in flexion. The Tl< demonstrates positional integrity to the base of the cervical curve. Malpositioning of the Tl< results in fixed flexion or extension of the cervical curve. Clinically, an increased flexion value would result in hyperlordosis of the lower cervical curve, while an increased extension value would result in hypolordosis of the cervical curve.

C2, C3, C4, C5, C6, C7 Disc<: (deg)

The disc angles are measured using the anterior and posterior disc heights. The measured disc angles are compared to ideal values of intact cervical curves with SV< greater than 38 degrees and less than 43 degrees. Clinically, a diminished angle results in anterior pillar loading, fixed flexion of the superior vertebra, fixed flexion of the CL<Rc and posterior joint instability, while an increased angle result in posterior pillar loading, fixed extension of the superior vertebra, fixed extension of the CL<Rc and excessive posterior joint loading.

In a similar manner, patient data points with respect to thoracic vertebrae are stored for retrieval to calculate the following lateral thoracic measurements:

LATERAL THORACIC MEASUREMENTS

Rc: Radius of Curvature; Overall (cm)

The radius is a measure of the thoracic curvature using three points located on the anterior superior body of T1, T6 and anterior inferior T12. Clinically, a loss of the curvature (increased radius of curvature, hypokyphotic) in combination with fixed regional extension, results in increased posterior pillar loading, while a gain in curvature (decreased Rc, hyperkyphosis) in combination with fixed regional flexion causes increased loading to the anterior pillar with separation of the posterior facets.

RcI: Radius of Curvature; Ideal (cm)

In the neutral position the ideal radius is calculated by equilibrating it to the chord distance from anterior/superior T1 to posterior/inferior T12.

RcU: Radius of curvature, Upper (cm)

The upper radius of curvature is measured using three points located on the anterior/superior body of T1, T3 and T6. The upper radius is compared to the ideal and measured radius. When the thoracic curve is coherent the upper radius approximates the measured (Rc) radius. Clinically, a difference in the upper radius to the measured radius is suggestive of the thoracic curve working as two separate units to accomplish regional and global compensation. An increased radius of curvature (hypokyphotic) causes increased posterior pillar loading. A decreased radius of curvature (hyperkyphotic) causes increased loading to the anterior pillar.

RcL: Radius of Curvature, Lower (cm)

The lower radius of curvature is measured using three points located on the anterior superior body of T7, T9 and T12. The lower radius is compared to the ideal and measured radius. When the thoracic curve is coherent the lower radius approximates the measured (Rc) radius. Clinically, a difference in the lower radius to the measured radius is suggestive of the thoracic curve working as two separate units to accomplish regional and global compensation. An increased radius of curvature (hypokyphotic) causes increased posterior pillar loading. A decreased radius of curvature (hyperkyphotic) causes increased loading to the anterior pillar.

CL<Rc: Centerline Angle of the Radius of Curvature (deg)

The centerline angle of the radius of curvature is a measure of fixed extension (+ angle) or flexion (− angle) of the thoracic curve. The curve centerline is drawn from the points (1) the curve focus and (2) the center of the curve. The curve centerline is compared to a horizontal. Clinically, fixed flexion of the centerline angle results in increased loading to the anterior pillar, while fixed extension of the centerline angle results in increased loading to the posterior pillar.

CL<RcU: Centerline Angle of the Upper Radius (cm)

The centerline angle of the upper radius of curvature is a measure of fixed extension (+) or flexion (−) of the upper thoracic curve. The curve centerline is drawn from the points; 1) the upper curve focus and 2) the center of the upper curve. The upper curve centerline is compared to a horizontal. Clinically, fixed flexion of the centerline angle results in increased loading to the anterior pillar, while fixed extension of the centerline angle results in increased loading to the posterior pillar.

CL<RcL: Centerline Angle of the Lower Radius (cm)

The centerline angle of the lower radius of curvature is a measure of fixed extension (+) or flexion (−) of the lower thoracic curve. The centerline is drawn from the points (1) the lower curve focus and (2) the center of the lower curve. The lower curve centerline is compared to a horizontal. Clinically, fixed flexion of the centerline angle results in increased loading to the anterior pillar. Fixed extension of the centerline angle results in increased loading to the posterior pillar.

SV<: Thoracic Stress Vertebra Angle (deg)

The stress vertebra line intersection is a measure of the integrity of the thoracic curve. Lines are drawn off the anterior vertebral body margins of T1 and T12. The normal angle of intersection is approximately 55–60 degrees. Clinically, diminished angulation (Hypokyphosis) results in increased posterior pillar loading, while increased angulation (hyperkyphosis) results in increased anterior pillar loading.

SV: Stress Vertebra (scale of 10 equal divisions)

The stress vertebra indicates the location of intersection of the thoracic stress lines. The normal intersection location is the T6/T7 disc interspace. The vertebra body is divided into 10 equal divisions and reported as ex. T4.9 (i.e., the line intersection occurs 9/10th of the way down the T4 vertebral body. Clinically, intersection of the thoracic stress lines other than T6/T7 indicates abnormal increased segmental loading at that location.

GT7: Gravity Transfer at T7 (mm)

GT7 is a horizontal measure of the body weight as it is projected vertically downward from the posterior superior body of T1 and compared to anterior superior body of T7. In an intact thoracic curve the body weight should pass anterior to the T7 reference point. Clinically, a horizontal measure passing posterior (+) to the T7 reference point indicates a disruption of the thoracic curvature or a centerline angle in fixed extension both of which cause posterior pillar loading to the lower thoracic and lumbar curves.

GT12: Gravity transfer at T12 (mm)

GT12 is a horizontal measure of the body weight as it is projected vertically downward from the posterior superior body of T1 and compared to posterior inferior body of T12. In an intact thoracic curve the body weight should pass through the reference point. Clinically, a horizontal measure passing posterior(+) to the T12 reference point indicates a disruption of the thoracic curvature or a centerline angle in fixed extension both of which cause increased posterior pillar loading to the lumbar spine.

T1<: T1 Angle (deg)

The parameter is essentially the same as the cervical T1<. The T1< is measured comparing a line drawn off the superior plate of T1 intersecting with a horizontal. The normal value is 30 degrees in flexion. The T1< demonstrates positional integrity to the base of the cervical curve. Malpositioning of the T1< results in fixed flexion or extension of the cervical curve. Clinically, an increased flexion value would result in hyperlordosis of the lower cervical curve, while an increased extension value would result in hypolordosis of the cervical curve.

T6<: T6 Angle (deg)

The T6 angle is measured drawing a line off the inferior plate of T6 and intersecting it with a horizontal. As this represents the inflection point of the thoracic curve the normal finding would be zero degrees. Clinically, a negative value (flexion) would force the upper thoracic curve into fixed flexion with resultant anterior pillar loading, while a positive value (extension) would force the upper thoracic curve into extension with resultant posterior loading to the lower thoracic and lumbar curves.

T12<: T12 Angle (deg)

The T12 angle is measured comparing a line drawn off the inferior plate of T12 and compared to a horizontal. The normal value is approximately 28 degrees. Clinically, a diminished value results in fixed flexion of the lower thoracic curve and increased anterior loading to the upper lumbar curve, while an increased value results in fixed extension of the lower thoracic curve and increases posterior loading to the upper lumbar curve.

Disc<: Disc angle; T1, T2, T3, T4, T5, T6, T7, T8, T9, T10, T11, T12 (deg)

The disc angles are measured using the anterior and posterior disc heights. Clinically, diminished angles result in anterior pillar loading, fixed flexion of the superior vertebra, fixed flexion of the CL<Rc and posterior joint instability, while increased angles result in posterior pillar loading, fixed extension of the superior vertebra, fixed extension of the CL<Rc and excessive posterior joint loading.

In a similar manner, patient data points with respect to lumbar vertebrae are stored for retrieval to calculate the following lateral lumbar measurements:

LATERAL LUMBAR MEASUREMENTS

Rc: Radius of Curvature, Overall/Measured (cm)

The radius of curvature is a measure of the lumbar lordosis using three points located on the anterior superior body of L1, L3 and L5. Clinically, a loss of the curvature (increased radius of curvature, hypolordotic) in combination with fixed regional flexion, results in increased anterior pillar loading and posterior joint separation, while an increase in the curvature (hyperlordotic) in combination with regional fixed extension, results in increased loading to the posterior pillar.

RcI: Radius of Curvature, Ideal

In the neutral position the ideal radius is calculated by equilibrating it to the chord distance from posterior/superior L1 to posterior/inferior S1.

RcU: Radius of curvature, Upper (cm)

The upper radius of curvature is measured using three points located on the anterior superior body of L1, L2 and L3. The upper radius is compared to the ideal and measured radius. When the lumbar curve is coherent the upper radius approximates the measured (Rc) radius. Clinically, a difference in the upper radius to the measured radius is suggestive that the lumbar curve is working as two separate units to accomplish regional and global compensation. Ligament instability or disruption is also suggested. An increased radius of curvature (hypolordosis) causes increased anterior pillar loading when combined with fixed flexion. A decreased radius of curvature (hyperlordosis) causes increased posterior loading when combined with fixed extension.

RcL: Radius of Curvature, Lower (cm)

The lower radius of curvature is measured using three points located on the anterior superior body of L4, L5 and S1. The lower radius is compared to the measured radius. When the lumbar curve is coherent the lower radius approximates the measured (Rc) radius. Clinically, a difference in the lower radius to the measured radius is suggestive that the lumbar curve is working as two separate units to accomplish regional and global compensation. Ligament instability or disruption is also suggested. An increased radius of curvature (hypolordosis) when combined with fixed flexion causes increased anterior pillar loading. A decreased radius of curvature (hyperlordosis) when combined with fixed extension causes increased posterior pillar loading.

CL<Rc: Centerline Angle of the Radius of Curvature (deg)

The centerline angle of the radius of curvature is a measure of fixed extension (+ angle) or flexion (− angle) of the lumbar curve. The curve centerline is drawn from the points; 1) the curve focus and 2) the center of the curve. The curve centerline is compared to a horizontal drawn through L3/4. Clinically, fixed flexion of the centerline angle results in increased anterior pillar loading and posterior joint separation. The pelvic extensors are in chronic reactive contraction, while fixed extension of the centerline angle results in increased posterior pillar loading. The pelvic flexors are in chronic reactive contraction.

CL<RcU: Centerline Angle of the Upper Radius (cm)

The centerline angle of the upper radius of curvature is a measure of fixed extension (+) or flexion (−) of the upper lumbar curve. The curve centerline is drawn from the points; 1) the upper curve focus and 2) the center of the upper curve. The upper curve centerline is compared to a horizontal. Clinically, fixed flexion of the centerline angle results in increased anterior pillar loading, while fixed extension of the centerline angle results in increased posterior pillar loading.

CL<RcL: Centerline Angle of the Lower Radius (cm)

The centerline angle of the lower radius of curvature is a measure of fixed extension (+) or flexion (−) of the lower lumbar curve. The centerline is drawn from the points; 1) the lower curve focus and 2) the center of the lower curve. The lower curve centerline is compared to a horizontal. Clinically, fixed flexion of the centerline angle results in increased anterior pillar loading, while fixed extension of the centerline angle results in increased posterior pillar loading.

SV<: Lumbar Stress Vertebra Angle (deg)

The stress vertebra line intersection is a measure of the integrity of the lumbar curve. Lines are drawn off the posterior vertebral body margins of L1 and L5 and the acute intersection angle measured. The normal intersection angle is approximately 35–38 degrees. Clinically, diminished angulation (Hypolordosis) results in increased anterior pillar loading when combined with fixed flexion, while increased angulation (hyperlordosis) results in increased posterior pillar loading when combined with fixed extension.

SV: Stress Vertebra (scale of 10 equal divisions)

The stress vertebra indicates the location of intersection of the lumbar stress lines. The normal intersection location is the L3/4 disc interspace. The vertebra body is divided into 10 equal divisions and reported as ex. L4.9 (i.e., the intersection occurs 9/10th of the way down the L4 vertebral body. Clinically, intersection of the lumbar stress lines other than the L3/4 interspace indicates abnormal increased segmental loading at that location.

GL4: Gravity Transfer at L4 (mm)

GL4 is a horizontal measure of the body weight as it is projected vertically downward from posterior superior body of L1 and compared to posterior superior L4. In an intact curve the body weight should pass posterior to the L4 reference point. Clinically, a horizontal measure passing anterior (−) to the reference point indicates a disruption of the lumbar curvature or a centerline angle in fixed flexion both of which cause increased anterior pillar loading to the lower lumbar curve.

GS1: Gravity Transfer at S1 (mm)

GS1 is a horizontal measure of the body weight as it is projected vertically downward from posterior superior body of L1 and compared to posterior superior S1. In an intact curve the body weight should pass through the reference point. Clinically, a horizontal measure passing posterior (+) to the S1 reference point indicates increased posterior pillar loading to the lumbar spine.

L1<: L1 Angle (deg)

A line is drawn off the inferior body of L1 and compared to a horizontal. The normal value would be approximately 27 degrees in extension. Clinically, a decreased value causes flexion of the lower thoracic curve and is usually associated with fixed flexion of the upper lumbar curve, while an increased value results in extension of the lower thoracic curve and is usually associated with increased posterior loading of the lumbar curve and sacroiliac joints.

L3<: L3 Angle (deg)

A line is drawn off the inferior body of L3 and compared to a horizontal. The reference position of zero is used in assessment. Clinically, an increased value results in extension of the upper lumbar spine and is usually associated with increased posterior pillar loading of the lumbar spine and sacroiliac joints, while a decreased value results in flexion of the upper lumbar curve and is usually associated with increased anterior pillar loading of the lumbar spine.

L5<: L5 Angle (deg)

A line is drawn off the inferior body of L5 and compared to a horizontal. The normal value is approximately 25 degrees in flexion. Clinically, a decreased negative (extension) value results in increased posterior pillar loading of the lumbar spine and sacroiliac joints, while an increased negative value (flexion) results in increased loading to the anterior pillar of the lumbar spine and sacroiliac joints.

Disc <: Disc angle L1, L2, L3, L4, L5

The disc angle is measured using the anterior and posterior disc height values. The measured DISC ANGLES are compared to ideal values of intact lumbar curves whose stress line angles measured between 35–43 degrees. Clinically, an increased angle results in fixed extension of the superior vertebra with resultant increased posterior pillar loading, while a decreased angle results in fixed flexion of the superior vertebra with resultant increased anterior pillar loading.

Appropriately selected ones of the above parameters can then be used to determine a spinal stress unit value for each of the three spinal regions. A proposed example thereof is shown in FIG. 17 wherein twenty-five of the cervical parameter measurements are used to determine a cervical spinal stress unit (SSU) value, which value is calculated from the absolute value of the differences of those parameters from an ideal value in each case. The determinations can be made at an initial patient examination before treatment (identified as "Pre") and after a first treatment (identified as "Post"). The cervical SSU value is the sum of the absolute values of such differences. The ideal values used therein were determined from a study of a relatively large number of patients having substantially intact cervical curves where the upper and lower radii of curvature were essentially coherent, i.e., there were no substantial distortions therein and they were within a normal range expected for uninjured patients. Thus, such ideal values were determined from X-rays in which the radii of curvatures of several of the cervices' of the patients involved were within 10 cm. of each other and in which the stress lines, i.e., the tangents at the ends of the cervical curve formed an angle between 38°–43°. With respect to such patients, the "ideal" parameters were determined by taking the statistical mean (frequency of occurrence) thereof.

As can be seen in FIG. 17 for the particular example depicted therein, the cervical SSU showed a reduction from 183.1 to 126.8 (i.e., a 31% change in a direction closer to the ideal). Still further comparable comparisons can be made over a series of treatment periods until the reduction in the SSU value becomes minimal, (i.e., no further reduction occurs) and treatment has proceeded to a point where further treatment will not result in further improvement.

Similar SSU values for the thoracic and lumbar regions can be calculated and a global SSU value can be calculated as the sum of each of the regional SSU values.

The sensitivity of the spinal problems that may exist in a patient can be assessed in a general way by assigning a severity scale corresponding to various ranges of the regional and global SSU values as set forth in FIG. 17. As can be seen in the particular example of FIG. 17, the initial (Pre) cervical SSU falls into a "very severe" range while the post cervical SSU falls into a "severe" range. Further treatment should reduce the values to more favorable severity ranges.

Accordingly, a patient's progress can be effectively evaluated using the above discussed parameters and the regional and global SSU values generated therefrom so that the practitioner can have a relatively objective technique for determining treatment progress and to determine when further treatment is either not needed and will result in no further improvement.

While the invention as discussed above represents a preferred embodiment of the technique of the invention, modifications thereof may occur to those in the art within the spirit and scope thereof. Hence, the invention is not to be construed as limited thereto, except as defined by the appended claims.

What is claimed is:

1. A computerized method for analyzing spinal characteristics of a patient believed to have one or more spinal abnormalities comprising the steps of:

creating a first data set by determining vertebral body rotations for a plurality of spinal vertebrae of the patient from anterior/posterior spinal x-rays of said patient, digitizing said first data set and inputting said digitized first data set into a data processing computer;

creating a second data set by determining vertebral body rotations for a plurality of spinal vertebrae of a normal person having no spinal abnormalities from anterior/posterior spinal x-rays of said patient, digitizing said second data set and inputting said digitized second data set into a data processing computer;

displaying the digitized vertebral body rotations of the patient in a graphical manner;

displaying the digitized vertebral body rotations of the normal person in a graphical manner;

comparing the digitized vertebral body rotations of the patient with the digitized vertebral body rotations of the normal person by processing the two sets of digitized data, determining the locations of spinal abnormalities of the patient; and providing readable output from said data processing computer regarding said locations of said spinal abnormalities.

2. A method in accordance with claim 1 wherein the vertebral body rotations of the patient and of the normal person are determined from x-rays taken in an anterior/posterior orientation.

3. A method in accordance with claim 2 wherein the differences between the vertebral body rotations of the patient and of the normal person are determined to be to the patient's left from the normal and/or to the patient's right from the normal.

4. A method in accordance with claim 1 wherein said displaying steps include displaying the vertebral body rotations of the patient and of the normal person in the form of horizontal bar graphs.

5. A method in accordance with claim 4 wherein the displaying steps further include displaying the vertebral body rotations of the patient and of the normal person in the form of tabular measurements.

6. A method in accordance with claim 4 wherein the horizontal bar graphs for the display of vertebral body rotations of the patient are displayed via the data processing computer adjacent to corresponding horizontal bar graphs for the display of vertebral body rotations for the normal person.

7. A method in accordance with claim 2 wherein the vertebral body rotations of the patient and of the normal person are determined as a distance D approximately corresponding to an arc length traversed by the interlamina junction of a vertebral body which is rotated from its theoretical center.

8. A method in accordance with claim 7 wherein the theoretical center of a vertebra is determined from said x-rays as the intersection location of diagonal lines drawn from opposing corners of the vertebra.

9. A method in accordance with claim 1 wherein said vertebral body rotations of the patient and the normal person are determined for spinal vertebrae in each of the cervical, thoracic and lumbar regions of the spine.

10. A method in accordance with claim 1 wherein said comparing step includes quantifying a rotational discontinuity of a vertebra with respect to its superior or inferior neighboring vertebra.

11. A method in accordance with claim 1 and further including determining the vertebral intersegmental rotational relationship between a vertebra and an adjacent vertebra for each vertebra of a plurality of spinal vertebrae of the patient.

12. A method in accordance with claim 11 and further including determining the difference between the relative rotational relationship of a vertebra and the relative rotational relationships of its superior neighboring vertebra; and displaying the differences for each vertebra of said plurality of vertebrae in a graphical manner;

determining the difference between the relative rotational relationship of a vertebra of said plurality of vertebrae and the relative rotational relationship of its superior neighboring vertebra for a normal person having no spinal abnormalities;

displaying the differences in a graphical manner;

comparing the differences determined for the patient with differences determined for the normal person to identify the locations of abrupt positional alignment changes representing spinal abnormalities in the patient.

13. A method in accordance with claim 12 and further including determining absolute values of the differences determined for each of the vertebra of the plurality of vertebrae of the patient;

adding the absolute values to provide numerical spinal stress unit scale numbers for each of the cervical, thoracic, and lumbar regions of the spine; and displaying said scale numbers for each of said regions.

14. A method in accordance with claim 13 and further including adding the scale numbers for each of said regions to provide a global spinal stress unit scale number; and displaying said global stress unit scale number.

15. A method in accordance with claim 14 and further including determining and digitizing regional stress unit scale numbers and global spinal stress unit scale numbers at a plurality of different successive times during treatment of the patient so as to track the progress of said treatment.

16. A method in accordance with claim 1 and further including creating a third data set by determining a disc angle for each vertebra of a plurality of vertebrae of the patient in the lateral dimension and digitizing said third data set;

displaying the determined disc angles of the patient via output from the data processing computer;

creating a fourth data set by determining a disc angle for each vertebra of said plurality of vertebrae of a normal person having no spinal abnormalities and digitizing said fourth data set;

displaying the determined disc angles of the normal person via output from the data processing computer; and by digital data processing of the third and fourth data sets comparing the determined disc angles of the patient and the determined disc angles of the normal person to determine any dissymmetries between corresponding vertebrae thereof.

17. A method in accordance with claim 16 wherein said disc angle determining steps include determining the disc angles of the patient and of the normal person when the spine is in a neutral and non-flexed, non-extended position.

18. A method in accordance with claim 17 and further including determining the disc angles of the patient and of the normal person when the spine is in a flexed position.

19. A method in accordance with claim 18 and further including determining the disc angles of the patient and of the normal person when the spine is in an extended position.

20. A method in accordance with claim 19 and further including by digital data processing of the two data sets comparing the disc angles of the patient and of the normal person in both the flexed position and the extended position.

21. A method in accordance with claim 20 and further including determining and digitizing as a data set the angular displacement changes in the disc angles from the neutral position to the flexed position for the patient and for the normal person;

determining and digitizing as a data set the angular displacement changes in the disc angles from the neutral position to the extended position for the patient and for the normal person; and comparing by digital data processing of the two data sets the angular displacement changes for the patient with the corresponding changes for the normal person to determine flexion and extension vertebral position deficiencies for the patient.

22. A method in accordance with claim 21 wherein the angular displacement values for the vertebrae are determined in each of the cervical, thoracic, and lumbar regions; and further including adding the angular displacement values for the vertebrae in each of said regions to obtain total angular displacement values for each of said regions.

23. A method in accordance with claim 22 and further including adding the total angular displacement values obtained for each of the cervical, thoracic, and lumbar regions to obtain a global angular displacement value.

24. A method in accordance with claim 1 and further including determining and digitizing as a data set from lateral x-ray images of the vertebrae of the cervical region of the patient a plurality of selected parameter values related to selected osseous landmarks at each vertebra;

making said parameter determinations for a patient prior to a treatment session and after a predetermined number of treatment sessions and by digital data processing of the two data sets determining the differences in said parameter values before and after said treatment sessions;

adding the absolute values of said differences for each of the selected parameters to provide an objective spinal stress unit value for said cervical region.

25. A method in accordance with claim 24 and further including determining said selected parameter values at successive treatment sessions for the patient and by digital data processing of the two data sets comparing the objective spinal stress unit values determined at subsequent treatment sessions with the values thereof determined at prior treatment sessions to track progress of the treatment of the patient over a course of said successive treatment sessions.

26. A method in accordance with claim 25 and further including determining and digitizing as a data set the objective spinal stress unit values for each of the thoracic and lumbar regions of the patient.

27. A method in accordance with claim 26 and further including adding the selected parameter values for each of the cervical, thoracic, and lumbar regions of the patient before and after treatment to determine a global objective spinal stress unit value.

28. A method in accordance with claim 27 and further including determining global objective spinal stress unit values for the patient at each of a plurality of successive treatment sessions to track progress of the patient over the course of said successive treatment sessions.

* * * * *